United States Patent
Moore et al.

(10) Patent No.: US 8,859,482 B2
(45) Date of Patent: Oct. 14, 2014

(54) METHOD FOR PREPARING A SOLID FORM OF ACETIC ACID AND PRODUCTS THEREOF

(75) Inventors: Ryan Giffin Moore, Lilburn, GA (US); Lucas John Smith, Powder Springs, GA (US)

(73) Assignee: ChemLink Laboratories, LLC, Kennesaw, GA (US)

( * ) Notice: Subject to any disclaimer, the term of this patent is extended or adjusted under 35 U.S.C. 154(b) by 13 days.

(21) Appl. No.: 13/371,631

(22) Filed: Feb. 13, 2012

(65) Prior Publication Data
US 2012/0208740 A1    Aug. 16, 2012

Related U.S. Application Data

(60) Provisional application No. 61/442,531, filed on Feb. 14, 2011.

(51) Int. Cl.
| | | |
|---|---|---|
| C07C 53/08 | (2006.01) | |
| C07C 53/10 | (2006.01) | |
| C12J 1/00 | (2006.01) | |
| C11D 7/08 | (2006.01) | |
| C11D 7/10 | (2006.01) | |
| C11D 11/00 | (2006.01) | |
| C11D 7/26 | (2006.01) | |
| C07C 51/02 | (2006.01) | |
| A01N 37/02 | (2006.01) | |

(52) U.S. Cl.
CPC ............... C11D 7/265 (2013.01); C07C 51/02 (2013.01); A01N 37/02 (2013.01)
USPC ........... 510/445; 510/477; 510/488; 510/494; 510/108; 510/180; 510/191; 510/238; 510/278; 562/607; 426/17

(58) Field of Classification Search
CPC ............ C12J 1/00; C07C 53/08; C07C 53/10; C07C 51/02; C11D 3/20; C11D 3/2079
USPC ......... 510/445, 477, 488, 494, 108, 180, 191, 510/238, 278; 562/607; 426/17
See application file for complete search history.

(56) References Cited

U.S. PATENT DOCUMENTS

| | | | | | |
|---|---|---|---|---|---|
| 2,696,441 | A | * | 12/1954 | Kmieciak et al. | 426/650 |
| 3,445,244 | A | * | 5/1969 | Noznick et al. | 426/103 |
| 3,898,344 | A | * | 8/1975 | Masuoka et al. | 426/124 |
| 3,920,586 | A | * | 11/1975 | Bonaparte et al. | 510/349 |
| 4,303,556 | A | * | 12/1981 | Llendado | 510/452 |
| 4,713,251 | A | * | 12/1987 | Seighman | 426/96 |
| 5,565,422 | A | * | 10/1996 | Del Greco et al. | 510/443 |
| 5,693,359 | A | * | 12/1997 | Wood | 426/650 |
| 6,039,881 | A | * | 3/2000 | Davies et al. | 210/732 |
| 2003/0032573 | A1 | * | 2/2003 | Tanner et al. | 510/400 |
| 2005/0101503 | A1 | * | 5/2005 | Caldwell et al. | 510/310 |
| 2005/0272820 | A1 | * | 12/2005 | Wheeler | 514/643 |

FOREIGN PATENT DOCUMENTS

| | | | | |
|---|---|---|---|---|
| DE | 3941994 | A1 | * | 6/1991 |
| JP | 51030160 | B | * | 8/1976 |
| JP | 76030160 | B | * | 8/1976 |
| JP | 60164475 | A | * | 8/1985 |

* cited by examiner

*Primary Examiner* — Lorna M Douyon

(74) *Attorney, Agent, or Firm* — McKenna Long & Aldridge LLP; Frank J. Miskiel; Matthew T. Bailey

(57) ABSTRACT

The present invention discloses a method of preparing a solid form of acetic acid. The method at least includes the steps of combining a solid acid and a metal acetate with a solvent to form a slurry. After a predetermined period of time, a solid form of acetic acid is recovered. The present invention also includes a solid product of acetic acid produced by the above-mentioned method. There is also disclosed a formulation including the solid product of acetic acid according to the present invention. Further, there is disclosed a cleaning system including the formulation according to the present invention.

15 Claims, No Drawings

METHOD FOR PREPARING A SOLID FORM OF ACETIC ACID AND PRODUCTS THEREOF

CROSS-REFERENCE TO RELATED APPLICATIONS

This application claims priority to U.S. Provisional Application Ser. No. 61/442,531 filed Feb. 14, 2011, which is incorporated by reference in its entirety.

FIELD OF INVENTION

The present invention generally relates to a method of producing a stabilized, solid form of acetic acid. The present invention also relates to a stabilized, solid form of acetic acid produced by the novel method of the present invention. The present invention also relates to a formulation comprise a stabilized, solid form of acetic acid.

BACKGROUND OF THE INVENTION

In the field of cleaning products, solid forms of disinfectants generally include at least pre-weighed powders and compressed tablets. Solid disinfectants are considered advantageous over their liquid counterparts. Specifically, solids require less packaging when transported from one location to another. Also, packaged solids weigh less than packaged liquids. Moreover, less storage space is required for packaged solids. Hence, solids are considered more economical with respect to shipment and storage of cleaning products compared to liquids. In addition, solid disinfectant products are safer to handle than liquid disinfectants. This is attributed to a liquid product's tendency to splash or spill during handling.

Preferably, organic acids are used as a cleaning product for producing solid cleaning products. In particular, vinegar has proven effective as a cleaning product given its strong antibacterial properties. Also, vinegar-based cleaning supplies have become an environmentally-friendly alternative to toxic cleaning supplies in view of global initiatives for reducing carbon footprint.

The main component of vinegar is acetic acid. Acetic acid is an organic compound having the chemical formula $CH_3COOH$. Generally, acetic acid is a weak acid. However, it can be corrosive in concentrated amounts. When undiluted, it is a colorless, corrosive, flammable liquid called glacial acetic acid. Acetic acid's chemical structure is shown below as formula (I).

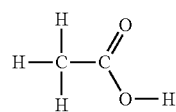

(I)

Organic acids, such as acetic acid, can be salted out of solution by various alkali metal and earth metal ions. By so doing, a dry form of acetic acid is produced. However, salting techniques can reduce, and even in some cases, eliminate the cleaning activity of the organic acid. Hence, this technique is considered unfavorable for producing cleaning solutions with a desired cleaning activity.

A need therefore exists in the art for a method of directly producing solid acetic acid.

A need also exists in the art for eliminating carbon footprint associated with toxic compounds in cleaning applications.

A further need exists in the art for an economically viable solid acetic acid useful for cleaning and/or disinfectant applications.

A further need exists in the art for a formulation including the solid acetic acid used for cleaning and/or disinfectant applications.

A further need exists in the art for a cleaning system including a formulation having a solid acetic acid.

SUMMARY OF THE INVENTION

A novel technique surprisingly has been conceived by the inventors for directly preparing a solid form of acetic acid. In particular, the inventors have utilized a pre-processing technique with reactants including a solid acid and a metal acetate in close proximity while applying high energy thereto. By so doing, solid acetic acid is produced in crystal form. The inventors also have surprisingly discovered how to manipulate the size of the solid crystallized form of acetic acid. In another embodiment, the crystal form of solid acetic acid is combined with other additives and ultimately processed into a compressed tablet or pre-weighed powder. Compressed tablets or pre-weighed powder preferably are used in disinfecting cleaning systems.

One advantage of the present invention is to provide an improved method for recovering stable, solid acetic acid.

A further exemplary advantage of the present invention is to provide an environmentally friendly, economical method of producing stable, solid acetic acid for cleaning and/or disinfectant applications.

A further yet exemplary advantage of the present invention is a stable, solid crystallized acetic acid produced by the novel pre-processing technique.

In an exemplary embodiment of the present invention, there is disclosed a method for preparing a solid form of acetic acid. The method includes a step of providing a solid acid. A metal acetate is combined with the solid acid to form a mixture. Then, a solvent is added to the mixture to form a slurry. Subsequently, the slurry is dried to recover a solid form of acetic acid. The solid acetic acid is a crystal.

In another exemplary embodiment of the present invention, there is disclosed a product of a solid, crystallized form of acetic acid. The product is produced by the method of combining a solid acid and metal acetate to form a mixture. A solvent is added to the mixture to form a slurry. Then, the slurry is dried to recover the solid, crystallized form of acetic acid.

In yet a further exemplary embodiment, there is disclosed a formulation comprising a solid form of acetic acid. The formulation includes other components. The formulation may include an effervescent compound. In an exemplary embodiment, the formulation is in the shape of a compressed tablet or powder. The formulation is particularly used for cleaning and/or disinfecting applications.

In yet even a further exemplary embodiment, there is disclosed a cleaning system comprising the formulation of the present invention. The cleaning system also includes a solvent for dissolving the solid form of the formulation. The cleaning system also includes a receptacle for containing the formulation and solvent.

It is to be understood that both the foregoing general description and the following detailed description are exemplary and explanatory and are intended to provide further explanation of the invention as claimed.

DETAILED DESCRIPTION OF THE PRESENT INVENTION

The inventors of the present invention have discovered a novel method for directly producing a stable, solid form of acetic acid. Namely, the stabilized form of the acetic acid is locked inside a crystalline salt neutralized form of the original acid. By so doing, a tablet or pre-weighed powder can ultimately be formulated incorporating the directly formed solid acetic acid crystal. The powders or tablets can be used in multi-purpose cleaning and/or disinfecting applications.

Specifically, the inventors have utilized a pre-processing technique requiring a close proximity and high energy system for ensuring a predetermined amount of acetic acid is produced. Namely, one (1) mol of acetic acid is produced for every one (1) mol of metal acetate reactant. In the preferred chemical reaction of the present invention, a proton of the dry acid has a high affinity for the acetate system. In addition, a salt ion of the acetate system has an affinity for the original acid. The overall rates of reaction vary with respect to the types of solid acids and metal acetate used in the reaction.

In the present invention, the terms solid and dry are synonymously used for describing acetic acid. Also in the present invention, the phrase stable compound is considered a compound that does not easily change or decompose into another compound. Cleaning activity is understood as the cleaning performance for removing undesired compounds from solid mediums to be cleaned, including but not limited to, metals, ceramics, glass, fibers.

In a preferred embodiment, a naturally existing solid acid is combined with a metal acetate to form a mixture. While continuously agitating the mixture, a solvent is added to produce a slurry. The slurry is continuously agitated during which time a chemical reaction occurs between the naturally existing solid acid and metal acetate. After a predetermined amount of time, the slurry is dried. The dried slurry includes a combination of a neutralized form of the original acid in crystalline form and a stabilized form of acetic acid locked inside the crystalline. The stable, solid acetic acid can thereafter be optionally processed by grinding it into a powder or granule.

In another exemplary embodiment of this invention, there is disclosed a more preferred method for producing a solid, stable form of acetic acid. Specifically, a naturally existing solid acid, such as citric acid, tartaric acid or sodium bisulfate, is combined with various salt neutralized acetates, such as sodium acetate, potassium acetate and silver acetate, to form a mixture. A desired amount of water is added to the mixture to form a paste or slurry. The paste is permitted to naturally air dry or alternatively, dry-assisted with the use of a heat source. The resulting product is a stable, solid form of acetic acid.

In yet another exemplary embodiment of the present invention, equal molar ratios of solid acid and metal acetate reactants are provided in the mixture. In an alternative embodiment, the solid acid and metal acetate are provided in different molar ratios. The molar ratio of solid acid to metal acetate can range anywhere from about 1,000:1 to 1:1. Preferably, the amount of solid acid molecules is in excess of the amount of metal acetate.

In yet a further embodiment of the present invention, during the step of adding a solvent to the mixture of a solid acid and a metal acetate system, full dissolution of the mixture is not required. That is, a solvent is proportionately added to the mixture to form a paste or slurry.

According to the present invention, the solid acids preferably used in the method are selected from citric acid, sodium bisulfate, malic acid, tartaric acid, fumaric acid, adipic acid, sulfamic acid or combinations thereof. In a preferred embodiment the solid acid is citric acid. Common in each of the above-mentioned solid acids is a hydrogen characterized as having a strong affinity for an acetate system.

According to the present invention, the metal acetates preferably used in combination with the solid acids described above acetic are selected from sodium acetate, silver acetate, potassium acetate, cupric acetate or combinations thereof. In a more preferred embodiment, sodium acetate or silver acetate are selected as the metal acetates. In an even more preferred embodiment, sodium acetate is the metal acetate.

In yet a further exemplary embodiment, an agitation technique can be used on the mixture of solid acid and metal acetate. A mixer, including but not limited to, an open top stand mixer preferably was used during bench-scale laboratory experiments. During scale-up for commercial purposes, a blender including, but not limited to, a vented, closed system vee blender, was preferably used. A two cubic foot vee blender was used in the experiments.

According the present invention, the mixture of solid acid and metal acetate was agitated for about 1 to about 20 minutes in normal atmospheric conditions. In a preferred embodiment, the solid mixture was agitated for about 5 to about 15 minutes. In yet even a more preferred embodiment, the solid mixture was agitated for about 5 to about 10 minutes.

According to the present invention, the preferred solvents used in combination with the above-mentioned mixture are selected from water, 1,2 propanediol, 1,3 propanediol, polypropylene glycol, ethanol, water-to-ethanol mixtures or combinations thereof. Water-to-ethanol mixtures can range anywhere from about 0.01:99.99 to about 50:50. Preferred ethanol-to water mixtures include, but are not limited to, 10:90, 20:80, 30:70, 40:60 and 50:50. In a more preferred embodiment, the solvent is water.

In an exemplary embodiment, the solvent is added to the dry mixture via a spray bottle to produce a slurry. While any type of spray bottle may be used for carrying out the method of this invention, such spray bottles should be large enough to capacitate an adequate amount of solvent for producing a slurry.

According to the inventors, the rate of reaction is dependent upon the amount and combination of solid acids and metal acetates. During the rate of reaction, the reactants were continuously agitated in a high energy system in close proximity. In an exemplary embodiment, the rate of reaction for about 15 total pounds of reactants including solid acid, metal acetate and water, was completed in about 20 to about 30 minutes.

After the reaction is complete, the slurry is allowed to dry. In a preferred embodiment, the slurry is air dried for a period of time ranging anywhere from about 24 to about 48 hours. Longer drying periods may be required if the slurry is not adequately dry. In an alternative embodiment, the slurry is forced dried using a heat source. In one embodiment, the slurry may be placed in trays with layers of slurry having a thickness less than or equal to 0.5 inches. The slurry is dried in a convection oven set at a temperature between about 60 to 70° C. The slurry is dried for about twenty minutes. Longer periods of drying may be necessary depending upon the wetness of the slurry.

According to the inventors of the present invention, reactions i. through vii as described in Table 1 are capable or producing a stable, solid acetic acid crystal. According to the stoichiometric equations, one acetic acid molecule is produced for every metal acetate molecule introduced into the reaction, i.e., 1:1 molar ratio. Each of the exemplary reactions i.-vii. will be explained in further detail below.

TABLE 1

| Reaction | Reactants |
|---|---|
| i. | $C_6H_8O_7 + CH_3COO^- Na^+ \to C_6H_8NaO_6 + CH_3COOH$ |
| ii. | $HNaO_4S + CH_3COO^- Na^+ \to Na_2O_4S + CH_3COOH$ |
| iii. | $C_4H_6O_5 + CH_3COO^- Na^+ \to C_4H_5NaO_5 + CH_3COOH$ |
| iv. | $C_4H_4O_4 + CH_3COO^- Na^+ \to C_4H_3NaO_4 + CH_3COOH$ |
| v. | $C_4H_6O_6 + CH_3COO^- Na^+ \to C_4H_5NaO_6 + CH_3COOH$ |
| vi. | $C_6H_{10}O_4 + CH_3COO^- Na^+ \to C_6H_9NaO_4 + CH_3COOH$ |
| vii. | Sulfamic Acid $H_3NO_3S + CH_3COO^- Na^+ \to H_2NaNO_3S + CH_3COOH$ |

In reaction i., citric acid and sodium acetate are reacted to produce sodium citrate and acetic acid. In each of the reactions ii. through vii, sodium acetate may be replaced with any other metal acetate, including but not limited to, cupric acetate, potassium acetate and silver acetate. For example, the reaction of citric acid reacts with silver acetate, produces silver citrate and acetic acid.

In reaction ii, sodium bisulfate is reacted with sodium acetate to produce sodium sulfate and solid acetic acid. In reaction iii., malic acid is reacted with sodium acetate to produce sodium hydrogen diglycolate and solid acetic acid. In reaction iv., fumaric acid is reacted with sodium acetate to produce sodium hydrogen fumarate and solid acetic acid. In reaction v., tartaric acid is reacted with sodium acetate to produce sodium hydrogen tartrate and solid acetic acid. In reaction vi., adipic acid is reacted with sodium acetate to produce sodium hydrogen adipate and solid acetic acid. In reaction vii, sulfamic acid is reacted with sodium acetate to produce sulpher sodium nitrate and solid acetic acid.

In another exemplary embodiment of the invention, an excess molar ratio of solid acid to metal acetate is preferred. As discussed above, the molar ratio of solid acid to metal acetate ranges from about 1:1 to about 10,000:1. The selection of the range is dependent upon many factors including, but not limited to, the final use of the resulting solid acetic acid crystal in formulation once diluted in an appropriate solution. The final use of the formulation may be for cleaning and/or disinfecting applications.

RESULTS AND DISCUSSION

In each of the examples described in Table 2 below, there is provided an amount of reactants necessary to produce a solid acetic acid for a particular cleaning application. Each of examples 1A-1C are conducted in a laboratory using an open top stand mixer. In each of laboratory examples 1A and 1B, the reactants include citric acid, silver acetate and water. Citric acid is considered useful in disinfecting applications. Laboratory example 1C includes reactants citric acid, sodium acetate and water. Example 1A is different from example 1B in view of the amount of water necessary to promote the reaction. Namely, example 1B has three times as much water as example 1A. The final crystal size is directly affected by water content. Thus, solid acetic acid produced via Example 1B will have larger crystals.

In comparison with examples 1A and 1B, the crystal size of acetic acid produced in Example 1C is much larger than the crystal size of acetic acid produced in examples 1A and 1B. Larger crystal size also is attributed to higher molar ratios of metal acetate with respect to the amount of solid acid. Example 1C has about eight times more metal acetate than examples 1A and 1B.

Examples 2A and 2B describe commercial production of solid acetic acid. Example 2A is different from 2B with regard to the ratio of citric acid to sodium acetate. Example 2A requires 10 pounds of citric acid and 1 pound of sodium acetate. On the other hand, example 2B requires 15 pounds of citric acid and 0.1 pounds of sodium acetate. Because the amount of water is equal in each of examples 2A and 2B, the particle size will be larger in example 2A in view of the larger metal acetate amount in the acid to metal acetate ratio.

TABLE 2

| Acetic acid Examples | Location | Blender | Acid | Salt | Solvent |
|---|---|---|---|---|---|
| 1A | Lab | Open top stand mixer | 289.5 g Citric Acid | 10.5 g Silver Acetate | 9 g water |
| 1B | Lab | Open top stand mixer | 289.5 g Citric Acid | 10.5 g Silver Acetate | 34 g water |
| 1C | Lab | Open top stand mixer | 192 g Citric Acid | 82 g Sodium Acetate | 9 g water |
| 2a | Production | V-Blender | 10 lbs Citric Acid | 1 lb. Sodium Acetate | 0.5 lbs water |
| 2b | Production | V-Blender | 15 lbs Citric Acid | 0.1 lb Sodium Acetate | 0.5 lbs water |

In an exemplary embodiment, an analysis of crystal size was performed using a column of sieves each with wire mesh cloth. This is also called a gradation test. Generally, a weighed sample is poured into the top sieve. The top sieve has the largest screen opening of all sieves. Each subsequently, lower placed sieve has smaller openings than the sieve located above it.

In one configuration, the stack of sieves in the column are placed in a mechanical shaker. The shaker agitates the column for a desired amount of time to facilitate gravitational separation of the larger crystal sizes from the smaller crystal sizes. The amount of sample retained at each sieve is divided by the total weight of the tested sample to determine the mean crystal sizes based on different mesh screen sizes of each sieve.

As shown in Table 3 below, solid forms of acetic acid are produced via reactants of citric acid and acetate. In a preferred embodiment, the acetate is sodium acetate or silver acetate. Each of the disclosed samples in Table 3 includes a column of sieves comprising four sieves and a pan. The sieves used in analyzing samples A-D are U.S. STD/ASTM E11 sizes. Specifically, the four sieve sizes include a 20 sieve, 40 sieve, 80 sieve and 100 sieve which are respectively equivalent to an 850 μm aperture, 425 μm aperture, 180 μm aperture and 150 μm aperture, i.e., British Standard.

Each of Samples A-D includes the reactants of citric acid, metal acetate i.e., sodium, silver, potassium or cupric and water. The product is formed by the reaction is acetic acid, a metal citrate i.e., sodium, silver potassium or cupric and citric acid. Silver acetate or cupric acetate are considered useful for disinfecting applications such as cleaning countertops or surfaces prone to bacteria likely from food and/or liquid particles.

According to Table 3, Sample B produced the largest mean crystal size. As discussed above, the largest crystal size is dependent upon the amount of water and the amount of acetate introduced into the chemical reaction. The largest mean crystal size was exhibited with a 20 sieve. Specifically, 62.4% of the total crystal product was maintained with a 30:1 citric to acetate ratio and 10% water. The crystal size of the crystals retained at a 20 sieve was approximately greater than or equal to 850 μm according to the screen mesh size.

Sample A exhibited the second largest mean crystal sized at a 40 sieve. The amount of total product maintained at a 30:1 citric to acetate ratio and 3% water was about 49.6% of the crystal product. The crystal size of the crystals retrieved at a 40 sieve approximately ranged from about 425 to about 850 μm.

Sample C exhibited a mean crystal size that was fairly similar to Sample A. Specifically, 48.1% of the total crystal product was retained at a 40 sieve. As such, the crystal size of the crystals retained at a 40 sieve approximately ranged from about 425 to about 850 μm.

Sample C exhibited the smallest mean crystal size of tested Samples A-D. Specifically, 54.2% of the total original crystal product was retained at a 60 sieve. Therefore, the crystal size of the crystals approximately ranged between about 180 and 425 μm. According to these results, the amount of acetate appears also to affect the mean crystal size in addition to water.

TABLE 3

| Sieve Size U.S. STD/ ASTM E11 | Sample A 30:1 Citric to Acetate-3% water | Sample B 30:1 Citric to Acetate-10% water | Sample C 100:1 Citric to Acetate-3% water | Sample D 100:1 Citric to Acetate-10% water |
| --- | --- | --- | --- | --- |
| 20 | 0.2% | 62.4% | 0.3% | 9.7% |
| 40 | 49.6% | 24.7% | 48.1% | 32.0% |
| 60 | 41.2% | 8.8% | 43.7% | 54.2% |
| 100 | 6.5% | 3.0% | 5.6% | 3.0% |
| Pan | 2.5% | 1.0% | 2.3% | 1.1% |

In yet even a further embodiment, a formulation including the solid acetic acid is combined with one or more additives. In an exemplary embodiment, the one or more additives are characterized as being compressible, free-flowing, concentrated, and non-sticky. These ingredients include, but are not limited to, surfactants, bleaching compositions, optical brighteners, anti-redeposition agents, chelating or sequestering agents, binders, lubricants, colors, and/or fragrances. The formulation may also include an effervescent. These ingredients may be used in any combination, depending on the purpose of the formulation.

The surfactants may include, but are not limited to, synthetic anionic surfactants which are generally water-soluble, alkali metal salts of organic sulfates and sulfonates. Alternatively, the surfactants may include non-ionic surfactants which are generally characterized as the reaction products of alkylene oxide with alkyl phenol or primary or secondary alcohols, amine oxides, phosphine oxides, dialkyl sulphoxides, amphoteric or zwitterionic surfactants, and/or soaps.

The bleaching compositions may include, but are not limited to, chlorinated isocyanurates, perborate hydrates, persulfates or percarbonates. Examples of the anti-redeposition agent may include, but are not limited to, acrylates and cellulose derivatives. The binder may include, but is not limited to, starch and starch derivatives, cellulose and cellulose derivatives, carbohydrate gums, sugars, resins, proteins and inorganic salts. The lubricant may include, but is not limited to, sodium benzoate, sodium stearate, magnesium stearate, aluminum stearate, stearic acid, mineral oil and polyethylene glycol, The effervescent used in the final formulation promotes the formation of bubbles in liquid environments. Additionally, the effervescent composition may also be capable of liberating carbon dioxide in or out of liquid environments.

In yet a further exemplary embodiment, the formulation having a solid acetic acid crystal further comprises at least the following additives: sodium bisulfate, sodium carbonate, sodium gluconate, polyethylene glycol and an acrylic acid homopolymer.

The final tablet formulation may include about 20 to about 50% of the crystal solid acetic acid discussed above. More preferably, the resulting crystal formation is about 30 to about 40% of the final tablet formulation. Even more preferably, the resulting crystal formulation is about 35 to about 38% of the final formulation. Specifically, the crystal includes solid acetic acid, metal citrate, and the remaining solid acid reactant. In a preferred embodiment, the crystal includes citric acid, monosodium citrate and acetic acid. Alternatively, the crystal includes citric acid, monosilver citrate and acetic acid.

Depending upon the desired, final application of the present invention, the formulation may be compressed and formed into tablets. Tablet size at least depends upon the ratio of dry acid amounts to acetate salts amounts. Tablet size may also depend upon the amount of water added to the mixture. For example, compressed tablets size may range anywhere from about 3 to about 60 grams by weight. In an exemplary embodiment, the tablet size ranges from about 10 to about 40 grams by weight. More preferably, the tablet size is about 20 grams by weight.

According to the spirit of the present invention, any tablet diameter may be used. In one embodiment, the tablets are greater than or equal to 1.75" in diameter. In another exemplary embodiment, the tablets are less than 1.75" in diameter.

In another exemplary embodiment, the final formulation may be in the form of a granule or granules. The granules may be uniform. Alternatively, the granules are non-uniform.

In yet another exemplary embodiment, the final formulation may be a powder. The powder generally includes fine particles typically smaller in particle size than granules.

APPLICATIONS OF THE FORMULATION

According to the present invention, the crystal product having acetic acid provided in a formulation may be used for cleaning applications such as hard surface cleaning, carpet cleaning, floor cleaning, glass cleaning, toilet bowl cleaning, tub and shower cleaning, hard water removal and soap scum removal.

In another embodiment, the present invention may be used for improving the luster of metals including, but not limited to, appliances such as dishwashers, microwaves, laundry machines and coffee makers. In addition, or alternatively, the present invention may be used for cleaning dishwashers, toaster ovens, convection ovens, gas ovens, electric ovens microwave ovens, laundry machines, coffee makers, specialty washers, i.e., baby bottle washers, and other household appliances that collect dirt and mildew during normal use. The present invention also is useful for cleaning glass and silver.

In a further embodiment, the invention may be used in disinfection technologies. In yet another embodiment, the invention may be used as a food additive where acidulation and vinegar are needed for food processing. In yet even a further embodiment, the present invention may be used in textile processing where an sour acid and acetic acid are needed to set dyes in fibers or for conditioning the product.

The final formulation, whether in the form of a tablet, granule or powder, may be dissolved in a liquid solution to form a cleaning solution. The liquid solution in the preferred embodiment is water, but may also be any liquid suitable for dissolving and using the cleaner of the present invention, including for example, but not limited to, an alcohol, e.g., low molecular weight alcohols such methanol, propanol and isopropanol; an aldehyde, e.g., formaldehyde or acetaldehyde;

or a ketone, e.g., a low molecular weight ketone such as acetone, methyl ethyl ketone, methyl isopropyl ketone, or methyl propyl ketone.

In an exemplary embodiment, the present invention may be used for dishwasher cleaning applications. Specifically, 20 grams of an effervescent tablet formulation containing solid acetic acid crystals is used. The tablet is dissolved less than about least first 5 minutes of contact with hot water. For the purposes of this invention, the term "hot" is understood as the average water temperature used in dishwashers. In this embodiment, the solid acetate to metal acetate ratio is 100:1. Other applications of the formulation, either in tablet or powder form can also be used in quick dissolving cleaning applications.

In yet a further exemplary embodiment of the present invention, there is disclosed a cleaning system including a formulation according to any of the above-mentioned embodiment. The cleaning system also includes a solvent for dissolving the formulation and a receptacle for containing the formulation and solvent. According to the present invention, the cleaning system may include any receptacle capable of containing a formulation and solvent. In particular, the receptacle may include spray bottles, sponges, mop buckets, bus tubs, or sinks It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A method for preparing a solid form of acetic acid, comprising:
    providing a solid acid;
    combining a metal acetate with the solid acid to form a mixture, wherein a molar ratio of the solid acid to the metal acetate is greater than 1:1;
    adding a solvent to the mixture to form a slurry in which the metal acetate is in close proximity to the solid acid to allow a chemical reaction to occur between the solid acid and the metal acetate;
    agitating the slurry for a time during which a chemical reaction occurs between the solid acid and the metal acetate; and
    drying the slurry to yield a composition comprising acetic acid inside a crystalline neutralized form of the solid acid.

2. The method of claim 1, wherein the molar ratio of the solid acid to the metal acetate is greater than or equal to 30:1.

3. The method of claim 1, wherein the solvent is added in an amount to prevent full dissolution of the mixture.

4. The method of claim 1, wherein the solid acid is selected from the group consisting of citric acid, sodium bisulfate, malic acid, tartaric acid, fumaric acid, adipic acid, sulfamic acid and combinations thereof.

5. The method of claim 1, wherein the metal acetate is selected from the group consisting of sodium acetate, silver acetate, potassium acetate, cupric acetate and combinations thereof.

6. The method of claim 1, wherein the solvent is selected from the group consisting of water, 1,2-propanediol, 1,3-propanediol, polypropylene glycol, ethanol, water-to-ethanol mixtures and combinations thereof.

7. The method of claim 1, wherein the drying of the slurry is by air drying without using a heat source.

8. The method of claim 1, wherein the drying of the slurry is by forced drying using a heat source.

9. The method of claim 1, wherein the drying of the slurry is by convection in an oven set at a temperature between about 60° C. to 70° C.

10. The method of claim 9, wherein the slurry is layered to a thickness of less than or equal to 0.5 inches.

11. A method for preparing a solid form of acetic acid, comprising:
    providing a solid acid;
    combining a metal acetate with the solid acid to form a mixture;
    adding a solvent to the mixture to form a slurry; and
    drying the slurry,
    wherein the molar ratio of the solid acid to the metal acetate is greater than or equal to 100:1.

12. The method according to claim 11, wherein the solid acid is selected from the group consisting of citric acid, sodium bisulfate, malic acid, tartaric acid, fumaric acid, adipic acid, sulfamic acid and combinations thereof.

13. The method according to claim 11, wherein the metal acetate is selected from the group consisting of sodium acetate, silver acetate, potassium acetate, cupric acetate and combinations thereof.

14. The method according to claim 11, wherein the solvent is selected from the group consisting of water, 1,2-propanediol, 1,3-propanediol, polypropylene glycol, ethanol, water-to-ethanol mixtures and combinations thereof.

15. The method of claim 11, wherein the solvent is added in an amount to prevent full dissolution of the mixture.

* * * * *

UNITED STATES PATENT AND TRADEMARK OFFICE
CERTIFICATE OF CORRECTION

| | | |
|---|---|---|
| PATENT NO. | : 8,859,482 B2 | Page 1 of 1 |
| APPLICATION NO. | : 13/371631 | |
| DATED | : October 14, 2014 | |
| INVENTOR(S) | : Moore et al. | |

It is certified that error appears in the above-identified patent and that said Letters Patent is hereby corrected as shown below:

IN THE CLAIMS:

Column 10, line 21 to line 23, should read:

--9. The method of claim 1, wherein the drying of the slurry is by convection in an oven set at a temperature between about 60° C to 70° C.--.

Signed and Sealed this
Twenty-seventh Day of January, 2015

Michelle K. Lee
*Deputy Director of the United States Patent and Trademark Office*